United States Patent [19]

Pissiotas et al.

[11] Patent Number: 4,490,167
[45] Date of Patent: Dec. 25, 1984

[54] OXIME DERIVATIVES OF DIPHENYL ETHERS AND THEIR USE IN HERBICIDAL COMPOSITIONS

[75] Inventors: Georg Pissiotas, Lörrach, Fed. Rep. of Germany; Otto Rohr, Therwil, Switzerland

[73] Assignee: Ciba-Geigy Corporation, Ardsley, N.Y.

[21] Appl. No.: 172,312

[22] Filed: Jul. 25, 1980

[30] Foreign Application Priority Data

Aug. 6, 1979 [CH] Switzerland .................... 7197/79

[51] Int. Cl.³ .................... A01N 37/34; C07C 121/60
[52] U.S. Cl. .................... 71/105; 260/465 D
[58] Field of Search .......... 260/465 F, 465 D, 465 E; 71/105

[56] References Cited

U.S. PATENT DOCUMENTS

| | | | |
|---|---|---|---|
| 3,234,255 | 2/1966 | Hackmann et al. | 260/465 D |
| 3,394,181 | 7/1968 | Bell | 260/465 F |
| 3,483,246 | 12/1969 | Kaufman | 260/465 D |
| 3,799,757 | 3/1974 | Dixon et al. | 71/76 |
| 3,822,314 | 7/1974 | Gay et al. | 260/465 E |
| 4,070,389 | 1/1978 | Martin | 260/465 E |
| 4,123,255 | 10/1978 | Freenor et al. | 260/465 E |
| 4,137,417 | 1/1979 | Hazama | 260/465 D |
| 4,152,137 | 5/1979 | Martin | 71/105 |
| 4,269,775 | 5/1981 | Szcepanski et al. | 260/340.7 |
| 4,353,736 | 10/1982 | Martin | 71/105 |

Primary Examiner—Ethel G. Love
Attorney, Agent, or Firm—Frederick H. Rabin

[57] ABSTRACT

The invention relates to novel oxime derivatives of diphenyl ethers of the formula

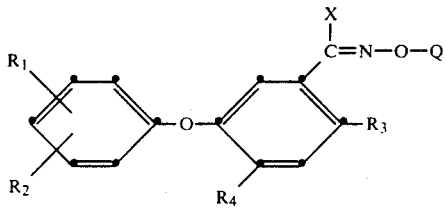

wherein Q is an aliphatic or araliphatic ether or ester radical, $R_1$ is halogen or a nitro, cyano or trifluoromethyl group, each of $R_2$ and $R_3$ is hydrogen, halogen or a nitro or cyano group, $R_4$ is hydrogen or halogen and X is hydrogen, halogen or a member selected from the group consisting of cyano, nitro, lower alkyl, lower alkanoyl, carboxylic acid lower alkyl ester or carboxamide. These compounds have good selective herbicidal action, they inhibit plant growth, and can be employed as safeners for protecting cultivated plants from the phytotoxic action of aggressive agrochemicals.

14 Claims, No Drawings

OXIME DERIVATIVES OF DIPHENYL ETHERS AND THEIR USE IN HERBICIDAL COMPOSITIONS

The present invention relates to novel oxime derivatives of diphenyl ethers, processes for their production, herbicidal compositions containing them, and their use as herbicides and plant growth regulators or safeners, i.e. antidotes for agrochemicals which, when applied alone, would cause phytotoxic damage to certain crops of useful plants.

Diphenyloxyalkanoic acids having herbicidal properties are known from the prior art (e.g. German Offenlegungsschrift Nos. 2 136 828 and 2 433 067), as are also herbicidal phenoxybenzoic acids (e.g. German Offenlegungsschrift No. 2 784 635). Diphenyloximes have recently been disclosed in Belgian Pat. No. 870 068. The oxime derivatives of diphenyl ethers of this invention are able to control e.g. weeds of the species Galium, Veronica and Viola in cereal crops. Up to now, such control has only been possible to an insufficient degree with selective herbicides.

Accordingly, the present invention provides oxime derivatives of diphenyl ethers of the formula

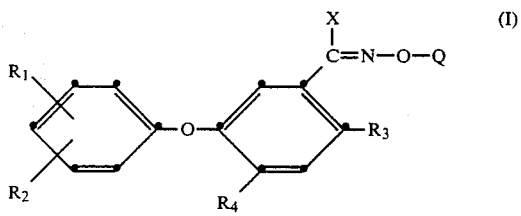

wherein $R_1$ is halogen or a nitro, cyano or trifluoromethyl group, each of $R_2$ and $R_3$ is hydrogen, halogen, or a nitro or cyano group, $R_4$ is hydrogen or halogen, X is hydrogen, halogen, or a member selected from the group consisting of cyano, nitro, lower alkyl, lower alkanoyl, carboxylic acid lower alkyl ester or carboxamide, Q is lower alkyl which is straight-chain or branched or which can be interrupted by heteroatoms or substituted by halogen; lower alkenyl or haloalkenyl; lower alkynyl; $C_3$–$C_7$cycloalkyl which is unsubstituted or substituted by halogen, or is lower cyanoalkyl; a lower alkanecarboxylic acid ester group, an alkanethiocarboxylic acid ester group, a lower alkanecarboxylic acid amide group; an aliphatic acyl radical; an araliphatic, cycloaliphatic or unsubstituted or substituted aromatic or heterocyclic acyl radical; an aliphatic, araliphatic, cycloaliphatic or unsubstituted or substituted aromatic or heterocyclic carbonic acid ester group; an alkylsulfonyl group; a sulfonamide group; or a carbamoyl radical.

By halogen in formula I is meant fluorine, chlorine, bromine or iodine.

The term "alkyl" by itself or as moiety of a substituent comprises branched or unbranched $C_1$–$C_8$alkyl groups. Lower alkyl denotes alkyl of 1 to 4 carbon atoms, for example: methyl, ethyl, propyl, isopropyl, butyl, sec-butyl, tert-butyl, and the higher homologues amyl, isoamyl, hexyl, heptyl, octyl together with the isomers thereof. By analogy, cyanoalkyl groups contain one additional carbon atom and alkanecarboxylic acid ester groups contain at least two additional carbon atoms.

Alkenyl radicals are aliphatic radicals containing one or also two double bonds (alkadienyls) and a maximum of 6, preferably 4, carbon atoms. Haloalkenyl radicals contain not more than 3 halogen atoms, preferably chlorine or bromine atoms. Alkynyl denotes propynyl (=propargyl) and butynyl.

Carboxamides comprise also monosubstituted or symmetrically or unsymmetrically disubstituted amides. The substituents can be selected from the group consisting of lower alkyl, lower alkenyl, propynyl or butynyl and also a phenyl ring which can be substituted or unsubstituted.

$C_3$–$C_7$Cycloalkyl groups are cyclopropyl, cyclobutyl, cyclopentyl, cyclohexyl and cycloheptyl. Cycloaliphatic radicals correspond to these ring systems, but, according to circumstances, can contain in addition one or more double bonds.

An araliphatic radical comprises an aryl group, such as unsubstituted or mono-, di- or trisubstituted phenyl, or also naphthyl, fluorenyl, or indanyl, which is bonded to the remainder of the molecule through lower alkyl or lower alkenyl. Examples are benzyl, phenethyl, phenylallyl and homologues.

Aromatic carboxylic acids are derived from aromatics, especially phenyl, and can be substituted. Heterocyclic carboxylic acids are derived from monocyclic or bicyclic rings containing 1 to 3 identical or different heteroatoms O, S and N. Mention may be made of heterocyclic ring systems having 3 to 6, especially 5 or 6, members, which can be saturated, partially saturated or unsaturated and can be substituted or unsubstituted. Without any limitation being implied, there may be mentioned as examples: furane, nitrofurane, bromofurane, methylfurane, thiophene, chlorothiophene, pyridine, 2,6-dichloropyridine, pyrimidine, pyridazine, pyrazine, piperidine, methylpiperidine, morpholine, thiomorpholine, tetrahydrofurane, oxazole, pyrazole, pyrrole, pyrroline, pyrrolidine, thiazole, 2,3-dihydro-4H-pyrane, pyrane, dioxane, 1,4-oxathi-(2)-ine.

Examples of aliphatic chains interrupted by heteroatoms are: methoxyethyl, ethoxyethyl, propoxyethyl, butoxyethyl, methoxypropyl, ethylthioethyl, methylaminoethyl, tertbutylaminoethyl, alkoxyalkoxyalkyl, such as methoxyethoxyethyl.

A carbamoyl radical (—CO—NH— or —CO—N<) carries at the nitrogen atom one or two radicals selected from the group consisting of lower alkyl, lower alkoxyalkyl, lower alkenyl, lower haloalkenyl, alkynyl or a hydrogen atom, and alternatively a $C_3$–$C_6$cycloalkyl ring or else a phenyl ring which is unsubstituted, or, as in the case of $R_2/R_3$, can be substituted.

Preferred compounds of the formula I are those wherein X is the cyano group and Q is an ester radical

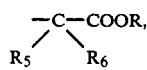

wherein R is lower alkyl, $R_5$ is hydrogen or lower alkyl, and $R_6$ is hydrogen, lower alkyl or lower alkoxy, $R_3$ is halogen, $R_4$ is hydrogen, and $R_1$ and $R_2$ are in the ortho- or para-position to the diphenyl ether bond.

In addition, $R_1$ is preferably p-$CF_3$ and $R_2$ is o-chlorine, i.e. the phenoxy radical has the structure

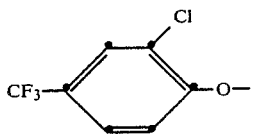

The compounds of the formula I are obtained by methods which are known per se.

In a first method, a halobenzene of the formula II

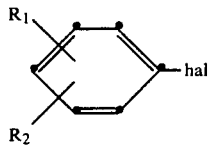

wherein $R_1$ and $R_2$ have the given meanings, is reacted with a m-hydroxybenzoate of the formula III

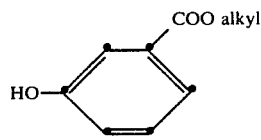

in the presence of a base, to give a diphenyl ether of the formula

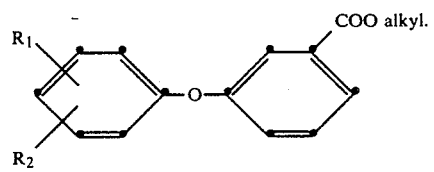

This diphenyl ether is treated, in an inert organic solvent, with lithium aluminium hydride or another reducing agent, until the ester group is reduced, to give a m-hydroxymethyl diphenyl ether of the formula V

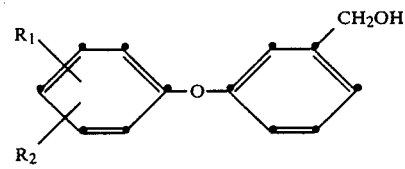

wherein $R_1$ and $R_2$ have the given meanings.

In this stage, the hydroxymethyl group is protected by esterification e.g. with a fatty acid, for example acetic acid, and then the substituents $R_3$ and, optionally, $R_4$ are introduced by nitration, halogenation, or optionally by reducing the nitro group to an amino group and replacing this latter by another substituent by means of a Sandmeier reaction, or also by reaction of a halogen substituent with potassium cyanide, to give a diphenylmethoxy ester of the formula VI

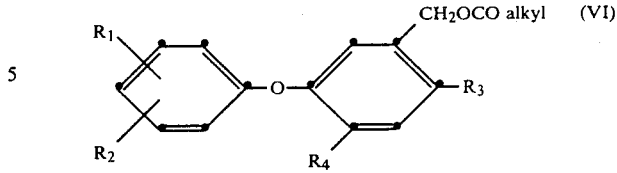

wherein $R_1$, $R_2$, $R_3$ and $R_4$ have the given meanings.

The fatty acid protective group is removed again by saponification with an inorganic base and the hydroxymethyl group is then converted with thionyl chloride or phosphoroxy chloride, or with thionyl bromide or phosphoroxy bromide, to the halomethyldiphenyl ether of the formula VII

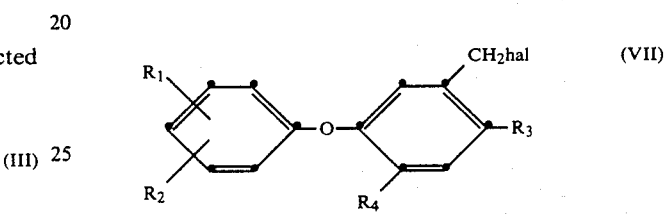

wherein hal is chlorine or bromine and $R_1$, $R_2$, $R_3$ and $R_4$ have the given meanings.

The halomethyldiphenyl ether of the formula VII is then converted with potassium cyanide or sodium cyanide to the corresponding cyanomethyl derivative ($-CH_2CN$). Reaction of this latter e.g. with pentyl nitrite ($C_5H_{11}ONO=O$), in the presence of sodium ethylate, yields an oxime salt of the formula VIII

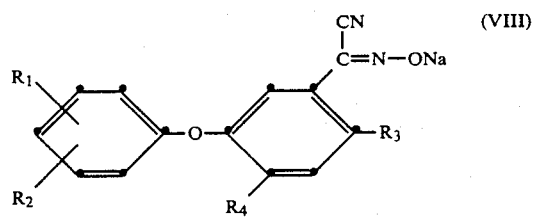

wherein $R_1$, $R_2$, $R_3$ and $R_4$ have the given meanings.

One process of this invention for producing the oxime ethers of the formula I comprises reacting the diphenyl ether oxime salt of the above formula VIII, in an inert organic solvent, with a compound of the formula IX

Y—Q                                                                          (IX)

wherein Y is a halogen atom or a removable acid radical and Q has the given meaning.

A further method of synthesising compounds of the formula I consists in reacting the halobenzene of the formula II, in an inert organic solvent and in the presence of a base, with a m-hydroxybenzaldehyde or a m-hydroxyphenylketone of the formula XI

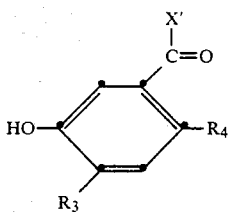

wherein X' is hydrogen or a lower alkyl radical and $R_3$ and $R_4$ have the given meanings, to give a diphenyl aldehyde or ketone of the formula XIII

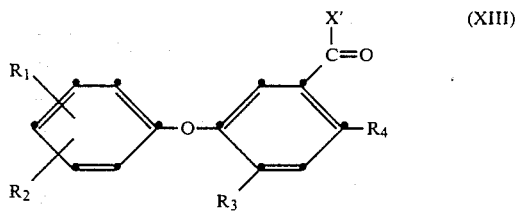

wherein X' is hydrogen or lower alkyl and $R_1$, $R_2$, $R_3$ and $R_4$ have the given meanings. This compound is converted with hydroxylamine ($NH_2OH$) to an oxime of the formula XIV

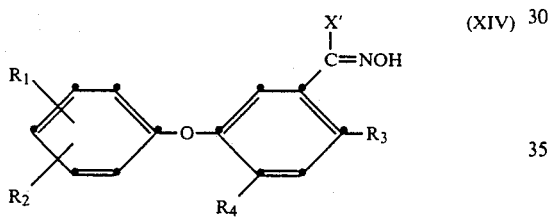

wherein $R_1$, $R_2$, $R_3$, $R_4$ and X' have the given meanings. This oxime is reacted with a compound of the formula IX, in an organic solvent and in the presence of a base, to give an oxime ether of the formula I, wherein X is hydrogen or lower alkyl. By reacting an oxime ether of the formula I, in which X is hydrogen, with corresponding reagents, it is possible finally to replace hydrogen by other radicals which fall under the definition of X.

These reactions are carried out in the temperature range from 0° to 150° C. and in suitable solvents such as acetone, methyl ethyl ketone, acetonitrile, dimethyl formamide, or dimethyl sulfoxide.

Suitable bases are both inorganic bases such as alkali metal hydroxides and carbonates and bicarbonates of alkali metals and alkaline earth metals, and also dry ammonia, as well as organic bases, e.g. tertiary lower alkylamines such as triethylamine, trimethylamine or also cyclic amines, e.g. pyridine, collidine, or also aromatic amines such as dimethyl aniline.

Removable acid radicals Y are e.g. an alkylsulfonyl group, an arylsulfonyl group, a nitro group, or a halogenated fatty acid radical, e.g. the radical of trichloroacetic acid.

These and other condensation reactions of α-oximino compounds and the alkali metal salts thereof with reactants Y—Q are described in "Organic Reactions", 1953, Vol. 7, pp. 343 and 373.

Oximes always exist in two stereoisomeric forms, the synform and anti-form. Throughout this specification, both stereoisomeric forms shall be understood as existing individually and as mixtures in any ratio.

The compounds (active ingredients) of the formula I are stable compounds which are soluble in conventional organic solvents, such as alcohols, ethers, ketones, dimethyl formamide, dimethyl sulfoxide etc.

The active ingredients of the formula I can be used by themselves, but more advantageously together with suitable carriers and/or other adjuvants, in the form of herbicidal compositions for controlling weeds.

In rates of application of 0.5 to 4 kg/hectare and more, the active ingredients and compositions which contain them have a pronounced herbicidal action especially on dicotyledonous weeds, such as Sida, Sesbania, Amaranthus, Sinapis, Ipomoea, Galium, Pastinak, Rumex, Matricaria, Chrysanthemum, Abutilon, Solanum etc. However, when employed in higher rates of application of at least 2 to 4 kg/hectare, a number of the active ingredients act on monocotyledonous weeds, such as Digitaria, Setaria and Echinochloa, whilst monocotyledonous cultivated plants, such as barley, wheat, maize, oats and rice, remain virtually undamaged at lower rates of application and suffer only minor damage at higher rates.

With these compounds, it has been possible to obtain good practical results in selectively controlling in particular dicotyledonous weeds in cereals, maize and rice. The most effective compounds have been found to be those having the structural formula

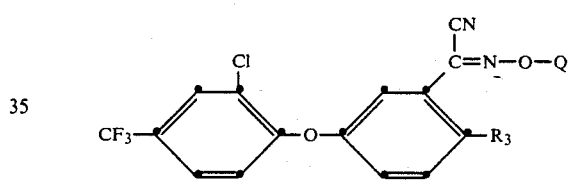

wherein $R_3$ is chlorine or nitro and Q is as defined for formula I.

The active ingredients and compositions containing them can be employed as contact herbicides in preemergence application to sown cultivated areas, but preferably in postemergence application to weed-infested crops of cultivated plants.

The compositions of the present invention are obtained in known maner by intimately mixing and grinding active ingredients of the general formula I with suitable carriers and/or adjuvants, with or without the addition of antifoam agents, wetting agents, dispersants and/or solvents which are inert to the active ingredients. The active ingredients can be processed to the following formulations:

solid formulations:

dust, tracking powders, granules (coated granules, impregnated granules and homogeneous granules), active ingredient concentrates which are dispersible in water:

wettable powders, pastes, emulsions, emulsifiable concentrates;

liquid formulations:

solutions.

The following Examples describe in more detail the production of the compounds of the invention, the preparation of ready-for-use solid and liquid formulations or active ingredient concentrates, and biological tests to determine herbicidal action. Parts and percentages are by weight and pressures are indicated in millibars.

EXAMPLE 1

Production of 2-chloro-5-(2'-chloro-4'-trifluoromethylphenoxy)phenyl-acetonitrile oxime (methoxycarbonyleth-1"-yl) ether (a) With stirring and under a nitrogen atmosphere, a solution of 45 g of methyl 3-(2-chloro-4-trifluoromethylphenoxy)benzoate (obtained by reaction of 3,4-dichlorobenzotrifluoride and methyl 3-hydroxybenzoate) in 60 ml of absolute ether is added dropwise at room temperature to a ready prepared mixture of 4 g of lithium aluminium hydride in 250 ml of absolute ether, such that the reaction mixture is kept moderately at the boil. When the addition is complete, stirring is continued for 1 hour under reflux. Remaining lithium aluminium hydride is destroyed by adding 5 ml of ethyl acetate and then a sufficient amount of 10% aqueous ammonium chloride solution is added dropwise until the formation of a readily filterable precipitate. After filtration, the ethereal phase is separated and the aqueous phase is extracted twice with ether. The combined ethereal phases are dried and then concentrated, affording 35.6 g of an oily product of the formula

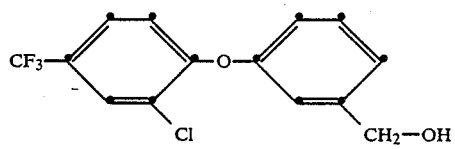

with a refractive index of $n_D^{25}$ 1.5424.

(b) Chlorine gas is introduced at a temperature of 20°–25° C. into a ready prepared mixture of 30.2 g of the compound obtained in (a) in 350 ml of glacial acetic acid until the starting material is consumed. The reaction mixture is then concentrated in vacuo and the oily residue is taken up in ether. The ethereal solution is washed twice with water, dried over sodium sulfate and concentrated, affording 38 g of a compound of the formula

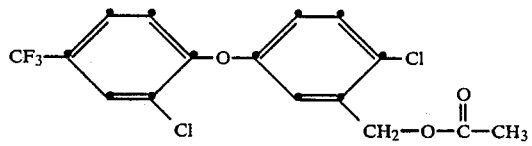

in the form of oil.

(c) 38 g of the acetate obtained in (b) is dissolved in 200 ml of methanol and the solution is reacted at room temperature for half an hour with 36 ml of 3.5N sodium hydroxide. After extraction with ether, the ethereal phase is washed three times with water, dried and concentrated, affording 32.5 g of the compound of the formula

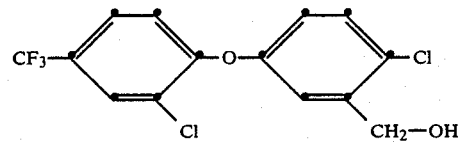

in the form of an oil with a refractive index of $n_D^{31}$ 1.5536.

(d) 4.5 ml of thionyl chloride are added dropwise at room temperature to a solution of 20 g of the alcohol obtained in (c) in 50 ml of toluene. After the evolution of gas has ceased, the reaction mixture is slowly heated and kept for 6 hours under reflux, then concentrated in vacuo, affording 20 g of the compound of the formula

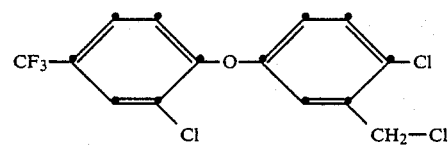

in the form of an oil.

(e) 20 g of the compound obtained in (d) are dissolved in 100 ml of dimethyl sulfoxide. With stirring, 9.4 g of sodium cyanide are added in portions, while keeping the temperature at 20°–25° C. The reaction mixture is then stirred for two hours and finally poured into ice-water and extracted with ether. The ethereal phase is washed three times with water, dried over sodium sulfate and concentrated, affording a product of the formula

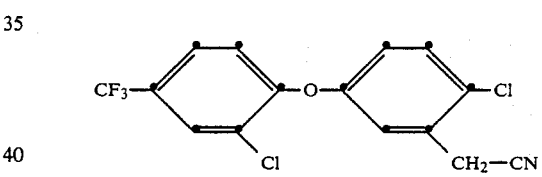

in a yield of 13.9 g and with a boiling point of 143° C./00.01 mbar.

(f) 11.4 g of the nitrile obtained in (e) are dissolved in a solution of 50 ml of ethanol and 2.3 g of sodium methylate, and then 4.4 ml of isopentyl nitrite are added dropwise at room temperature. The reaction mixture is stirred overnight and the product is precipitated with 100 ml of hexane. The precipitate is collected by filtration, affording 9.3 g of a product of the formula

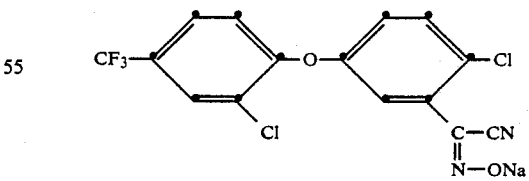

(g) 9.3 g of the sodium salt of the oxime obtained in (f) are dissolved in 50 ml of dimethyl formamide, and then 4 g of methyl 2-bromopropionate are added dropwise at room temperature. After stirring for 12 hours, the reaction mixture is poured into water and extracted with ether. The ethereal solution is dried over sodium sulfate and concentrated, affording 8.5 g of the compound of the formula

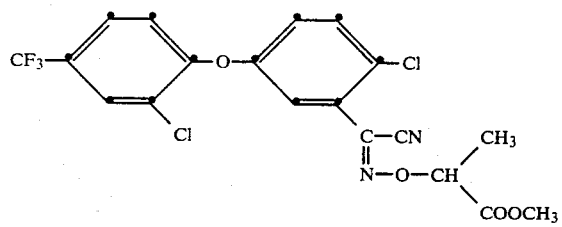

in the form of an oil with a refractive index of $n_D^{24}$ 1.5392.

The following table lists further compounds which are obtained in analogous manner:

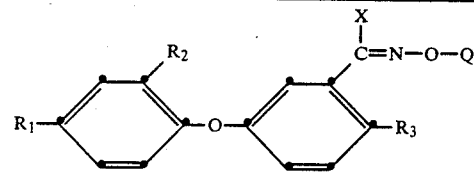

| Compound | R₁ | R₂ | R₃ | X | Q | |
|---|---|---|---|---|---|---|
| 1 | CF₃ | Cl | Cl | CN | CH(CH₃)COOCH₃ | $n_d^{23}$ 1.5392 |
| 2 | CF₃ | Cl | Cl | CN | CH(CH₃)COOC₂H₅ | $n_D^{24}$ 1.5310 |
| 3 | CF₃ | Cl | Cl | CN | CH(CH₃)COOC₄H₉n | $n_D^{24}$ 1.5254 |
| 4 | CF₃ | Cl | Cl | CN | CH(CH₃)COOC₄H₉iso | $n_D^{24}$ 1.5220 |
| 5 | CF₃ | Cl | Cl | CN | CH(CH₃)COOCH₂—C≡CH | $n_D^{24}$ 1.5458 |
| 6 | CF₃ | Cl | Cl | CN | SO₂N(CH₃)₂ | |
| 7 | CF₃ | Cl | Cl | CN | SO₂CH₃ | |
| 8 | CF₃ | Cl | Cl | CN | SO₂CH₂—C₆H₅ | |
| 9 | CF₃ | Cl | Cl | CN | CH(CH₃)COOC₂H₄N(CH₃)₂ | |
| 10 | CF₃ | Cl | Cl | CN | CH(CH)₃COOC₅H₁₁iso | |
| 11 | CF₃ | Cl | Cl | CN | CH₂CN | $n_D^{31}$ 1.5490 |
| 12 | CF₃ | Cl | Cl | CN | CH(CH₃)CN | $n_D^{31}$ 1.5365 |
| 13 | CF₃ | Cl | Cl | CN | CH₂COOCH₃ | $n_D^{24}$ 1.5425 |
| 14 | CF₃ | Cl | Cl | CN | —CH(CH₃)(OCH₃)—COOCH₃ | $n_D^{31}$ 1.5265 |
| 15 | Cl | Cl | Cl | CN | CH(CH₃)COOCH₂CH=CH₂ | |
| 16 | Cl | Cl | Cl | CN | COC₆H₅ | |
| 17 | Cl | Cl | Cl | CN | CONHC₆H₅ | |
| 18 | Cl | Cl | Cl | CN | CH₂CONH₂ | |
| 19 | Cl | Cl | Cl | CN | CH(CH₃)COONH₂ | |
| 20 | CF₃ | NO₂ | Cl | CN | CH(CH₃)COOC₃H₇n | |
| 21 | CF₃ | NO₂ | Cl | CN | CH(CH₃)COOC₄H₉n | |
| 22 | CF₃ | NO₂ | Cl | CN | CH(CH₃)COOCH₂—CH=CH₂ | |
| 23 | CF₃ | NO₂ | Cl | CN | CH(CH₃)COOCH₂—C≡CH | |
| 24 | CF₃ | NO₂ | Cl | CN | CH(CH₃)COOCH₂CH(CH₃)C₃H₇ | |
| 25 | CF₃ | NO₂ | Cl | CN | CH₂COOCH₃ | |
| 26 | CF₃ | NO₂ | Cl | CN | CH₂COOCH₃ | |
| 27 | CF₃ | NO₂ | Cl | CN | SO₂CH₂—C≡CH | |
| 28 | CF₃ | NO₂ | Cl | CN | SO₂CH₂—CH₂=CH₂ | |
| 29 | CF₃ | NO₂ | Cl | CN | CON(CH₃)₂ | |
| 30 | CF₃ | NO₂ | Cl | CN | CONHCH₃ | |
| 31 | CF₃ | Cl | NO₂ | CN | CH(CH₃)CN | |
| 32 | CF₃ | Cl | NO₂ | CN | CH(CH₃)COOCH₃ | |
| 33 | CF₃ | Cl | NO₂ | CN | CH(CH₃)COOC₄H₉n | |
| 34 | CF₃ | Cl | NO₂ | CN | CH(CH₃)CONH₂ | |
| 35 | CF₃ | Cl | NO₂ | CN | CH(CH₃)CON(CH₃)₂ | |
| 36 | CF₃ | Cl | NO₂ | CN | CH(CH₃)COOCH₂C≡CN | |
| 37 | CF₃ | Cl | NO₂ | CN | CH(CH₃)SO₂N(CH₃)₂ | |
| 38 | CF₃ | Cl | NO₂ | CN | CH(CH₃)SO₂CH₂C₆H₅ | |
| 39 | CF₃ | Cl | NO₂ | CN | COONHC₆H₅ | |
| 40 | CF₃ | Br | NO₂ | CN | CH₂COOCH₃ | |
| 41 | CF₃ | Br | Cl | CN | CH₂COOC₂H₅ | |
| 42 | CF₃ | Br | Cl | CN | CH(CH₃)COOCH₃ | |
| 43 | CF₃ | Br | Cl | CN | CH(CH₃)CONHCH₃ | |
| 44 | CF₃ | Br | Cl | CN | CH(CH₃)COOCH₂C₆H₅ | |
| 45 | CF₃ | Br | Cl | CN | CH(CH₃)CONHC₆H₄Cl(para) | |
| 46 | CF₃ | Br | Cl | CN | CH(CH₃)CONHC₆H₃Cl(3',4') | |
| 47 | CF₃ | Br | Cl | CN | CH(CH₃)CON(CH₃)OCH₃ | |
| 48 | CF₃ | Br | Cl | CN | CH(CH₃)COOC₅H₁₁iso | |
| 49 | CF₃ | Br | Cl | CN | CH(CH₃)COOC₄H₉sec | |
| 50 | CF₃ | Br | Cl | CN | CH(CH₃)COOC₃H₇iso | |
| 51 | Cl | Cl | NO₂ | CN | CH(CH₃)CONHC₆H₄CH₃(3') | |
| 52 | Cl | Cl | NO₂ | CN | CH(CH₃)CONHC₆H₄Cl(4') | |
| 53 | Cl | Cl | NO₂ | CN | CH(CH₃)CON(CH₃) | |
| 54 | Cl | Cl | NO₂ | CN | CH(CH₃)SO₂CH₃ | |
| 55 | Cl | Cl | NO₂ | CN | CH(CH₃)SO₂CH₂C₆H₅ | |
| 56 | Cl | Cl | NO₂ | CN | CH(CH₃)SO₂CH₂C≡CH | |
| 57 | Cl | Cl | NO₂ | CN | CH(CH₃)COOCH₃ | |

-continued

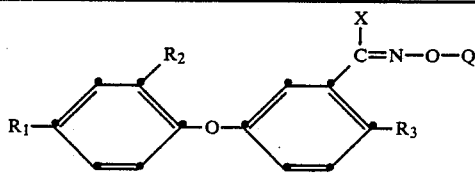

| Compound | R₁ | R₂ | R₃ | X | Q | |
|---|---|---|---|---|---|---|
| 58 | Cl | Cl | NO₂ | CN | CH(CH₃)COOC₂H₅ | |
| 59 | Cl | Cl | NO₂ | CN | CH(CH₃)COOC₂H₄N(CH₃)₂ | |
| 60 | Cl | Cl | NO₂ | CN | CH(CH₂)COOC₄H₉n | |
| 61 | CF₃ | Cl | CN | CN | CH₂COOCH₃ | |
| 62 | CF₃ | Cl | CN | CN | CH₂COOC₂H₅ | |
| 63 | CF₃ | Cl | CN | CN | CH(CH₃)COOCH₃ | |
| 64 | CF₃ | Cl | CN | CN | CH(CH₃)COOC₂H₅ | |
| 65 | CF₃ | Cl | CN | CN | CH(CH₃)CONH₂ | |
| 66 | CF₃ | Cl | CN | CN | CH(CH₃)CON(CH₃)₂ | |
| 67 | CF₃ | Cl | CN | CN | CH(CH₃)CONHC₆H₅ | |
| 68 | CF₃ | Cl | CN | CN | CN(CH₃)CONHC₆H₄CF₃(3′) | |
| 69 | CF₃ | Cl | CN | CN | CH(CH₃)SO₂CH₃ | |
| 70 | CF₃ | Cl | CN | CN | CH(CH₃)SO₂N(CH₃)₂ | |
| 71 | CF₃ | CN | Cl | CN | CH(CH₃)COOCH₃ | |
| 72 | CF₃ | Cl | Cl | CN | CH(CH₃)COOH | resin |
| 73 | CF₃ | Cl | Cl | CN | CH(C₂H₅)COOH | resin |
| 74 | CF₃ | Cl | Cl | CN | CH₂COOH | resin |
| 75 | CF₃ | Cl | Cl | CN | CH(CH₃)COOC₃H₇n | $n_D^{31}$ 1.5243 |
| 76 | CF₃ | Cl | Cl | CN | CH(CH₃)COOC₃H₇iso | $n_D^{31}$ 1.5181 |
| 77 | CF₃ | Cl | Cl | CN | CH(CH₃)COOC₄H₉sec | $n_D^{31}$ 1.5165 |
| 78 | CF₃ | Cl | Cl | CN | CH(CH₃)COOC₂H₄OCH₃ | $n_D^{28}$ 1.5249 |
| 79 | CF₃ | Cl | Cl | CN | CH(CH₃)CONHC₂H₄OCH₃ | $n_D^{40}$ 1.5387 |
| 80 | CF₃ | Cl | Cl | CN | CH(CH₃)COOCH₂CH=CH₂ | $n_D^{24}$ 1.5418 |
| 81 | CF₃ | Cl | Cl | CN | CH(C₂H₅)COOCH₃ | $n_D^{24}$ 1.5368 |
| 82 | CF₃ | Cl | Cl | CN | CH(C₂H₅)COOC₂H₅ | $n_D^{25}$ 1.5303 |
| 83 | CF₃ | Cl | Cl | CN | CH(C₂H₅)COOCH(CH₃)CH₂OCH₃ | $n_D^{28}$ 1.5235 |
| 84 | CF₃ | Cl | Cl | CN | CH(C₂H₅)CN | $n_D^{30}$ 1.5493 |
| 85 | CF₃ | Cl | Cl | CN | CH(C₃H₇n)COOCH₃ | $n_D^{23}$ 1.5357 |
| 86 | CF₃ | Cl | Cl | CN | CH(C₂H₅)COOC₃H₇n | $n_D^{25}$ 1.5293 |
| 87 | CF₃ | Cl | Cl | CN | CH(C₂H₅)COOC₄H₉n | $n_D^{25}$ 1.5240 |
| 88 | CF₃ | Cl | Cl | CN | CH(CH₃)COSCH₃ | $n_D^{25}$ 1.5642 |
| 89 | CF₃ | Cl | Cl | CN | CH(CH₃)COSC₂H₅ | $n_D^{25}$ 1.5570 |
| 90 | CF₃ | Cl | Cl | CN | CH(CH₃)COSCH₂CH=CH₂ | $n_D^{24}$ 1.5623 |

EXAMPLE 2

Preparation of ready-for-use solid and liquid formulations and active ingredient concentrates Granules The following substances are used to formulate 5% granules:

5 parts of an active ingredient of the formula I,
0.25 part of epoxidised vegetable oil,
0.25 part of cetyl polyglycol ether
3.50 parts of polyethylene glycol,
91 parts of kaolin (particle size 0.3–0.8 mm).

The active ingredient is mixed with epoxidised vegetable oil and the mixture is dissolved in 6 parts of acetone; the polyethylene glycol and cetyl polyglycol ether are then added. The resultant solution is sprayed on kaolin, and the acetone is subsequently evaporated in vacuo.

Wettable Powder

The following constituents are used to formulate (a) a 70% and (b) a 10% wettable powder:

(a)

70 parts of an active ingredient of the formula I,
5 parts of sodium dibutylnaphthylsulfate,
3 parts of naphthalenesulfonic acid/phenolsulfonic acid/formaldehyde condensate (3:2:1),
10 parts of kaolin,
12 parts of Champagne chalk;

(b)

10 parts of an active ingredient of the formula I,
3 parts of a mixture of the sodium salts of saturated fatty alcohol sulfates,
5 parts of naphthalenesulfonic acid/formaldehyde condensate,
83 parts of kaolin.

The respective active ingredient is applied to the corresponding carriers (kaolin and chalk) and then these are mixed and ground, to yield wettable powders of excellent wettability and suspension power. By diluting these wettable powders with water it is possible to obtain suspensions containing 0.1 to 80% of active ingredient. These suspensions are suitable for controlling weeds in cultivations of plants.

Paste

The following substances are used to formulate a 45% paste:

45 parts of an active ingredient of the formula I,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol, 23 parts of water.

The active ingredient is intimately mixed with the additives in appropriate devices and ground. By diluting the resultant paste with water, it is possible to prepare suspensions of the desired concentration.

Emulsifiable Concentrate

The following ingredients are mixed to formulate a 25% emulsifiable concentrate:
  25 parts of an active ingredient of the formula I,
  5 parts of a mixture of nonylphenolpolyoxyethylene and calcium dodecylbenzenesulfonate,
  15 parts of cyclohexanone,
  55 parts of xylene.

This concentrate can be diluted with water to give emulsions in suitable concentrations of e.g. 0.1 to 10%.

EXAMPLE 3

Test methods for determining the herbicidal action

Pre-emergence herbicidal action (germination inhibition)

In a greenhouse, seeds of test plants are sown in flower pots having a diameter of about 15 cm, such that 12–25 plants can develop in each pot. Directly after sowing, the flower pots are treated with an aqueous suspension of active ingredient obtained by diluting an active ingredient concentrate with water. The concentration of active ingredient is calculated such that it can be expressed in kg per hectare. The pots are then kept in the greenhouse under the same constant conditions (22°–25° C., 50–70% relative humidity, and regular watering). The test is evaluated after 21 days and the condition of the plants is noted. In rates of application of 1 kg/ha and more, all the tested compounds are very effective against the dicotyledonous plants and weeds.

Post-emergence herbicidal action (contact herbicide)

Seeds of both monocotyledonous and dicotyledonous plants and weeds are sown in a greenhouse in flower pots of about 13 cm diameter, such that 12–25 plants are able to develop in each pot. The plants are allowed to germinate and, when they have reached the 4–6 leaf stage after about 2 weeks, they are treated with an aqueous active ingredient suspension. The suspension is obtained by diluting an active ingredient concentrate with water. The amount of active ingredient applied is such that the concentration can be expressed in kg per hectare. After the treatment, the pots are kept in the greenhouse under the same conditions as in the pre-emergence test. The test is evaluated 15 days after treatment and the condition of the plants is noted. In this test, the test compounds have severely damaged in particular the dicots. Some plants are damaged even at low rates of application of 0.5 kg/ha.

In a field test, the compound of Example 1, 2-chloro-5-(2'-chloro-4'-trifluoromethylphenoxy)phenylacetonitrile oxime(methoxycarbonyl-1"-alkyl)ether, when employed as selective herbicide in rates of application of 1 and 2 kg, destroys persistent weeds of the species Galium, Veronica and Viola in wheat.

What is claimed is:

1. A compound of the formula

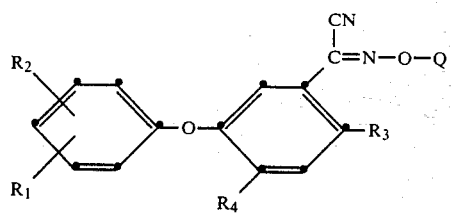

wherein
  $R_1$ is halogen, nitro, cyano or trifluoromethyl,
  $R_2$ is hydrogen, halogen, nitro or cyano,
  $R_3$ is halogen, nitro or cyano,
  $R_4$ is hydrogen or halogen, and
  Q is lower alkanecarboxylic acid ester or lower alkanethiocarboxylic acid ester.

2. A compound of the formula

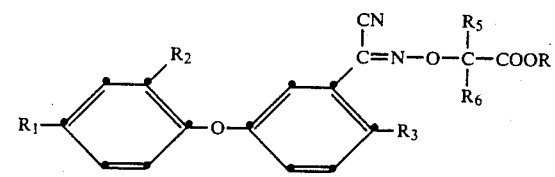

wherein
  $R_1$ is halogen, nitro, cyano or trifluoromethyl,
  $R_2$ is hydrogen, halogen, nitro or cyano,
  $R_3$ is halogen,
  R is lower alkyl,
  $R_5$ is hydrogen or lower alkyl, and
  $R_6$ is hydrogen, lower alkyl or lower alkoxy.

3. A compound according to claim 1 of the formula

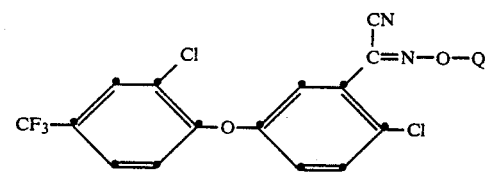

wherein Q is as defined in claim 1.

4. A compound according to claim 2 of the formula

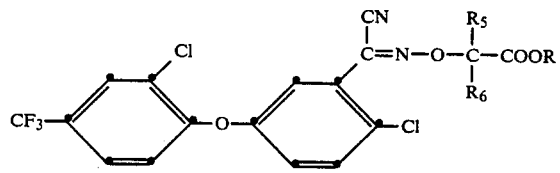

wherein R, $R_5$ and $R_6$ are as defined in claim 2.

5. An oxime derivative of a diphenyl ether according to claim 1 of the formula

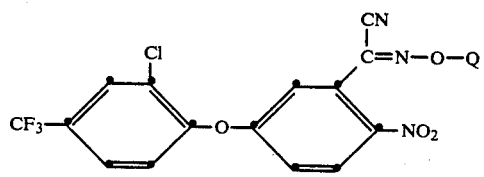

wherein Q is as defined in claim 1.

6. The compound according to claim 3 which is 2-chloro-5-(2'-chloro-4'-trifluoromethylphenoxy)-phenylacetonitrile oxime methoxycarbonyl-eth-1"-yl ether.

7. The compound according to claim 3 which is 2-chloro-5-(2'-chloro-4'-trifluoromethylphenoxy)-phenylacetonitrile oxime isobutyloxycarbonyl-eth-1"-yl ether.

8. The compound according to claim 3 which is 2-chloro-5-(2'-chloro-4'-trifluoromethylphenoxy)-phenylacetonitrile oxime methylthiocarbonyl-eth-1"-yl ether.

9. The compound according to claim 3 which is 2-chloro-5-(2'-chloro-4'-trifluoromethylphenoxy)-phenylacetonitrile oxime ethoxycarbonyl-eth-1"-yl ether.

10. The compound according to claim 3 which is 2-chloro-5-(2'-chloro-4'-trifluoromethylphenoxy)-phenylacetonitrile oxime n-butoxycarbonyl-eth-1"-yl ether.

11. The compound according to claim 4 which is 2-chloro-5-(2'-chloro-4'-trifluoromethylphenoxy)-phenylacetonitrile oxime methoxycarbonyl-eth-1"-methoxy-1"-yl ether.

12. A herbicidal composition which comprises a herbicidally effective amount of at least one oxime derivative of a diphenyl ether according to claim 1 or 2, and a carrier.

13. A method of selectively controlling weeds in crops of cultivated plants, which comprises applying to said crops a herbicidally effective amount of a compound according to claim 1 or 2.

14. A method of selectively controlling weeds in cereals crops, which comprises applying to said crops a herbicidally effective amount of a compound according to claim 1 or 2.

* * * * *